United States Patent [19]

Reno

[11] 4,038,147

[45] July 26, 1977

[54] METHOD FOR DETECTING ENDOTOXINS

[75] Inventor: Woodrow James Reno, Baltimore, Md.

[73] Assignee: Becton, Dickinson and Company, Rutherford, N.J.

[21] Appl. No.: 696,429

[22] Filed: June 15, 1976

[51] Int. Cl.$^2$ .................. G01N 31/00; G01N 33/16
[52] U.S. Cl. ..................... 195/103.5 R; 23/230 B;
195/103.5 A; 195/103.5 M; 424/2
[58] Field of Search ............... 195/103.5 R, 103.5 A,
195/103.5 M; 424/2; 23/230 B

[56] References Cited

U.S. PATENT DOCUMENTS

| | | | |
|---|---|---|---|
| 3,179,567 | 4/1965 | Owren | 195/103.5 R |
| 3,395,210 | 7/1968 | Lenahan et al. | 195/103.5 R X |
| 3,486,981 | 12/1969 | Speck | 195/103.5 R X |
| 3,915,805 | 10/1975 | Levin | 195/103.5 R |
| 3,947,378 | 3/1976 | Babson | 195/103.5 R X |
| 3,960,669 | 6/1976 | Innerfield | 195/103.5 R |

*Primary Examiner*—David M. Naff
*Attorney, Agent, or Firm*—Kane, Dalsimer, Kane, Sullivan and Kurucz

[57] ABSTRACT

A rapid and reliable method is disclosed for determining the presence or absence of endotoxins in solution, including biological liquids such as transudates and exudates. The method comprises a procedure based upon the alteration of a modified coagulation test system by endotoxins produced by gram-negative microorganisms. The method is particularly useful as reliable aid in the early diagnosis and treatment of infections caused by gram-negative microorganisms and to alert the diagnostician to the possibility of septic shock in an infected host.

9 Claims, 1 Drawing Figure

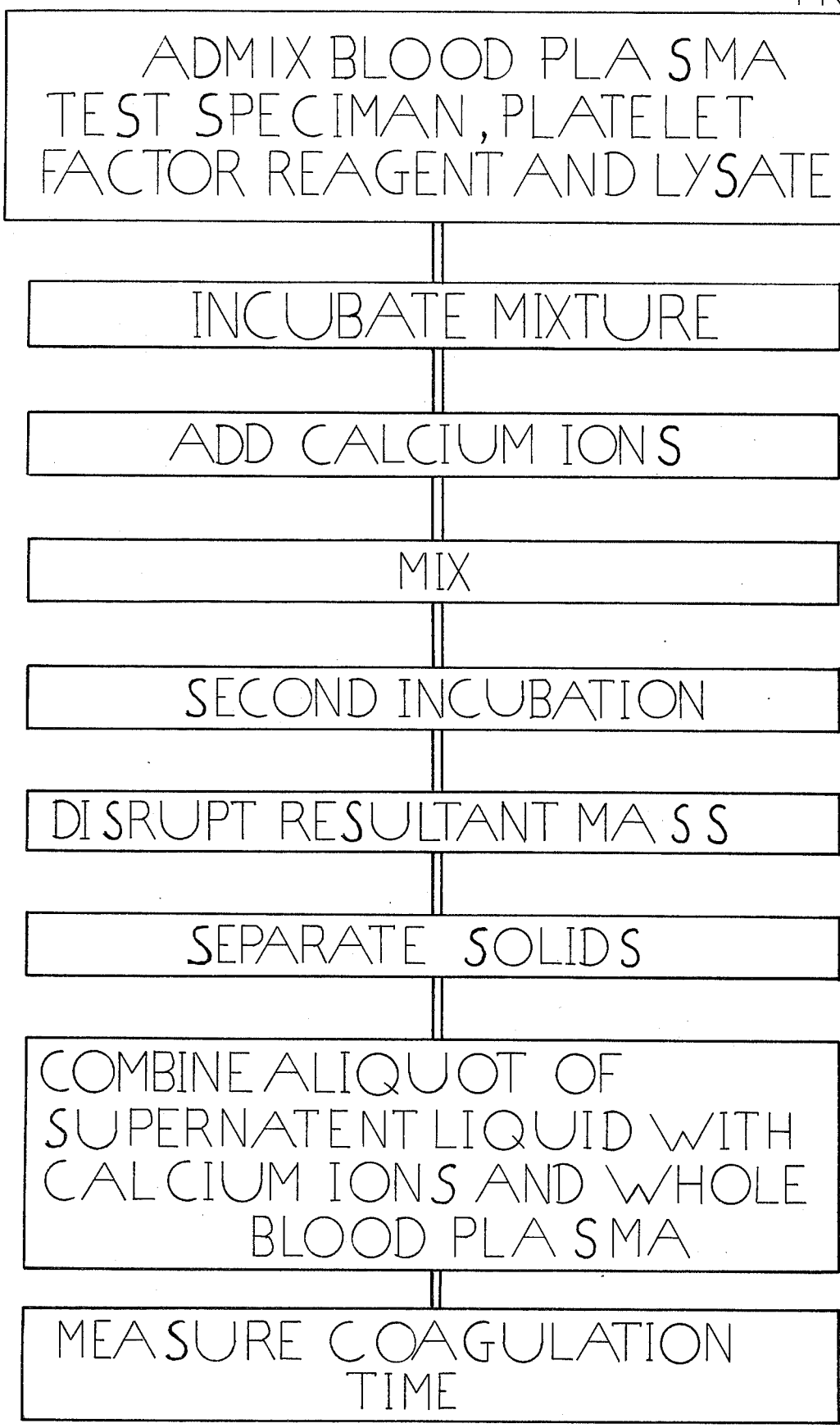

METHOD FOR DETECTING ENDOTOXINS

BACKGROUND OF THE INVENTION

1. Field of the Invention

The invention is related to the detection of lipopolysaccharide-polypeptide macromolecules or portions thereof in solution and more particularly is related to methods of detecting endotoxins of gram negative organisms in fluids including biological liquids.

2. Brief Description of the Prior Art

Gram-negative septic shock is a possibly fatal development in mammals who suffer burns, undergo surgery and/or contract fulminating infections. Present theory is that at least four basic physiologic defects are associated with localized or disseminated gram-negative sepsis in humans, which differentiate the conditions from conditions of similar symptomology. These defects are an infectious process, hypotension, hypoxia and intravascular coagulation.

The condition of septic shock can develop very rapidly, often in a matter of hours to a point of irreversibility. Septic shock has poor prognosis, the survival rate being something less than 30 to 40%. When the condition of septic shock progresses to the point where a circulatory collapse is manifested by symptoms of such collapse, only about 25% of the victims survive.

For the above reasons, it is of vital importance that diagnostic tools be made available which will reliably and rapidly confirm the presence or absence of endotoxins in solutions, particularly biological fluids such as blood serum, spinal fluid, urine, saliva, pus and like materials. Time is of the essence if appropriate treatment for septic shock is to be undertaken. Accordingly, any method which provides an advantage of speed, even minutes, is of great potential value provided the method has a high degree of accuracy.

It is also of great commercial importance to make available rapid, economic, simple and reliable test procedures for the detection of endotoxins as indicative of the presence of gram-negative microorganisms in foodstuffs, pharmaceuticals, industrial fermentations and like materials.

Prior to my invention, it was known that the lysate extracted from the amebocytes of Limulus polyphemus (the horseshoe crab) coagulated in the presence of endotoxins. This knowledge was the basis of a number of methods disclosed for the detection of endotoxins. For example, in the Journal Laboratory of Clinical Medicine, 78 (1), pages 136–148, (July, 1971), Cooper et al discloses the detection of endotoxin in fluids by first admixing the test fluid with Limulus amebocyte lysate. The mixture is incubated at 37° C. for from 4 to 6 hours and then at room temperature for up to 20 hours. The mixture of incubate is observed every 15 minutes during the initial 4 to 6 hour incubation period and thereafter periodically for a total of 24 hours. Development of an increase in turbidity or viscosity of the mixture is a positive sign of endotoxin presence. Similarly, Hochstein et al., Bulletin of the Parenteral Drug Association, 27 (3): 139, discloses the detection of endotoxins by admixing a test fluid with Limulus amebocyte lysate and incubating the mixture for 60 minutes at 37° C. At the end of this period, gelation of the mixture is said to be a positive indication of the presence of endotoxin.

Reinhold et al. reported in Proc. Soc. Exp. Biol. and Med., 137: 334, (1971) an improved method of detecting endotoxins in blood plasma. The improved method comprises first treating the unknown plasma with acid to obtain a pH of 4.0 and then adjusting with buffer to a pH of 6.2. The unknown specimen is then diluted with normal saline. To the treated plasma there is then added a proportion of Limulus amebocyte lysate and the resulting mixture is incubated for 60 minutes at 37° C. Gelation of the mixture during this period is said to be indicative of endotoxin presence.

Additional teachings of the art, generally cumulative to the above, may be found for example in Levin et al., Thrombos Diathes. Haemorrh., 19 186, (1968); Levin et al., Bulletin of John Hopkins Hospital, 115: 265, (1964); Jorgensen et al., Pro. Soc. Exp. Biol. and Med., 146: 1024-31, (1974); Wildfeuer, App. Microbiol., 28: (5): 867–71, (November, 1974); Levin et al., J. Lab. Clin. Med., 75 (6): 903,–911; Eibert, Bulletin of the Parenteral Drug Association, 26 (5): 253–260; Jorgensen et al., Applied Microbiology, 26 (1): 38–42; and Nachum et al., New England Journal of Medicine, 289 (18) 931–934, (Nov. 1, 1973).

In general, the prior art methods have required long incubation times and/or given results which are difficult to interpret, i.e.; depend upon the observation of a degree of viscosity or turbidity for a positive indication of the presence of endotoxins. A difficulty of interpretation, does not lend accuracy and reliability to the methods of the prior art. The prior art methods also leave an open question as to the exact end point of the test procedures, i.e.; a question as to the proper length of time for incubation beyond which any coagulation of the test material may be discounted as due to causes other than the presence of endotoxins.

By the method of my invention, rapid results may be obtained with clear indications of positive or negative presences of endotoxin. The method of my invention is simple to carry out, does not require extensive training, may be performed with a minimum of laboratory apparatus, gives a high degree of reproducible and reliably accurate results and is highly sensitive to even minimal quantities of endotoxins.

SUMMARY OF THE INVENTION

The invention comprises a method of determining the presence or absence of endotoxins in liquids, which comprises;

a. admixing aliquots of mammalian blood plasma, mammalian blood platelet factor reagent, Limulus polyphemus amebocyte lysate and the liquid for determination;

b. incubating the mixture obtained in (a) above;

c. admixing a source of calcium ions with the incubated mixture of (b) above;

d. incubating the mixture of (c) above;

e. disrupting the mixture obtained by incubating in (d) above;

f. separating solids from the disrupted mixture to obtain a supernatant;

g. mixing aliquots of the supernatant, a source of calcium ions and mammalian blood plasma;

h. measuring the elapsed time between the completion of mixing in step (g) above and coagulation of the mixture obtained thereby; and i. comparing the elapsed time measured in step (h) above with the elapsed time measured after following the steps (a) through (h) above but replacing the liquid for determination added in step (a) with an equal proportion of a known endotoxin free solution.

The method of the invention is useful for detecting endotoxins in solution and consequently for determining the presence of gram-negative toxins. The method of the invention is particularly advantageous as a rapid means for assisting in the diagnosis of bacterial infections due to gram-negative microorganisms.

BRIEF DESCRIPTION OF THE DRAWINGS

FIG. 1 is a process flow chart showing a preferred embodiment of the invention.

DETAILED DESCRIPTION OF THE INVENTION

The method of the invention may be conveniently followed by referring to the process flow chart shown in FIG. 1. In the first step, a mixture is prepared from platelet factor reagent, mammalian blood plasma, lysate reagent and the specimen of liquid to be tested for the presence of endotoxin. Admixture may be carried out in conventionally employed pyrogen free laboratory vessels, preferably with the homogeneous blending offered by the use of a Vortex mixer.

In the preferred embodiments of the invention, the proportion of reagents and unknown in the first step differ slightly depending upon the nature of the unknown liquid specimen. More specifically, when the unknown material is a liquid other than blood serum, the plasma is first diluted in a ratio of from 1:4 to 1:10 (v/v) with an aqueous buffer solution. For the detection of endotoxins in blood serum, the plasma is first diluted in a ratio of from 1:4 to 1:15 with the aqueous buffer solution, preferably 1:10 (v/v). The diluted plasma is then mixed with the platelet factor (0.1 - 0.5 ml/ml. of diluted plasma), lysate (0.1 - 0.4 ml/ml. of diluted plasma) and 0.1 to 0.5 ml. of the unknown solution, (preferably 0.2 ml.). The plasma employed when testing blood serum specimens should be an adsorbed plasma, i.e.; blood plasma treated with barium sulfate to adsorb blood factors II, VII, IX and X.

In the second step of the method of the invention, the mixture obtained as described above is incubated at 37° C. for 10 minutes. Following the incubation, calcium ions may be added to the incubated mixture by introduction of a calcium salt solution such as aqueous calcium chloride. The proportion of calcium solution used is from about 0.1 to 0.3 ml. per ml. of diluted plasma of a 0.001 to 0.5 molar solution. In the next step of the preferred method of the invention, the incubated mixture with calcium ions added is homogeneously mixed and then incubated a second time. In the case of a non-blood serum specimen, the incubation is carried out at 37° C. for 5 to 30 minutes, preferably about 20 minutes. If the unknown test specimen is blood serum, the incubation should be extended for an additional 5 minutes to total about 15 to 35, preferably about 15 minutes of incubation. Following the second incubation, it will be noted that the incubate comprises an agglomerated mass in liquid suspension. This mass is disrupted by vigorous agitation, preferably with a Vortex mixture and the resulting mixture is separated to remove solids. Preferably, separation is effected with the assistance of an applied centrifugal force. To complete the method of the invention, an aliquot of the supernatant liquid is admixed with a source of calcium ions and a substantially equal volume of whole blood plasma. The proportion of calcium components in the final mixture is advantageously in the range of from about 0.1 to 0.5 ml. of a 0.001 to 0.5 molar solution of calcium salt to 0.1 ml. of the supernatant. Upon completion of the admixture, the mixture is observed for coagulation. The time required for coagulation is noted. When negative toxins are present in the unknown specimen, coagulation generally occurs within about 60 to 80 seconds of the final admixture, when the test specimen is blood serum and within 40 to 60 seconds when the test specimen is a liquid other than blood serum. However, coagulation itself is not a positive indicator of the presence of endotoxins by the method of the invention. For a positive determination, the above described procedure is repeated completely but with replacement of the unknown liquid specimen with an equal volume of an appropriate liquid known to be free of endotoxins, i.e.; a negative control. This provides a standard for comparison of coagulation times. To determine the presence of endotoxin in the unknown, the coagulation time observed for the unknown is compared to the coagulation time for the negative control standard. If the coagulation time for the unknown shows an increase of 20 to ± 100% of the coagulation time for the negative control, endotoxins are positively present. If the coagulation time is less than a 20% increase of the negative control, endotoxins are not present in the unknown specimen.

Platelet factor reagent, (partial thromboplastin) is a rabbit brain extract prepared according to the method of Bell and Alton. It is a standardized source of platelet factor substitute commercially available in a lyophilized form from the BBL Division of Bioquest, Division of Becton, Dickinson and Company, Cockeysville, Md.

Adsorbed plasma reagent is a source of factors V (labile factor), VIII (anti-hemophilic factor), XI (plasma thromboplastin antecedent) and XII (Hageman factor) and fibrinogen prepared by adsorption of factor II (prothrombin), VII (proconvertin), IX (plasma thromboplastin) component and X (Stuart-Prower factor) from normal mammalian blood plasma with barium sulfate. The lyophilized reagent represents a 1 to 5 dilution and is available from BBL supra.

The following examples and preparations describe the manner and process of making and using the invention and set forth the best mode contemplated by the inventor of carrying out the invention, but are not to be construed as limiting.

PREPARATION 1

N-ethyl maleimide Solution

A $1 \times 10^{-2}$ Molar solution of N-ethyl maleimide is prepared by dissolving 1.25 grams of N-ethyl maleimide in 1 liter of sterile, pyrogen free 3 percent saline.

PREPARATION 2

Limulus Polyphemus Amoebocyte Lysate

In the following preparation, all glassware is made pyrogen-free and sterilized by heating at 370° F. for about 3 hours in a dry oven.

One hundred milliliters of blood is drawn directly from Limulus polyphemus (horseshoe crab) into siliconized Ehrlenmeyer flasks previously charged with 100 ml. of warm (circa 40° C) N-ethyl maleimide solution prepared according to Preparation 1, supra, freshly prepared on the day of use. The resulting mixture is stirred gently and then allowed to stand for about 90–120 minutes. During this period the amebocytes settle to the bottom. The supernatent is removed by aspiration and the cells, which appear creamy white, are then gently resuspended using a small amount of 3% saline which has been warmed to circa 40° C.

The resuspended cells are then placed in siliconized centrifuge tubes and spun as slowly and for as short a time as possible to produce a soft button. The cells are then washed twice with 3% saline at a temperature of 40° C. It is not necessary to pre-heat the centrifuge tubes or to maintain the centrifuge at 40° C. Following the second saline wash, approximately 10-15 ml. of sterile pyrogen-free distilled water is injected into the tube by use of a needle and syringe to produce an approximate ratio of 1:5 between cells and lysing agent. The resulting mixture is then agitated with the use of a Vortex mixer, or similar equipment. The tube is covered tightly because any contamination at this stage will result in an unsuccessful preparation. The resulting material is severely re-agitated approximately 1 hour later and then approximately twice daily until 48 hours have elapsed. During this period, the siliconized tubes in which the amebocytes are disrupting are kept at room temperature. At the end of this 48 hours, the material is centrifuged to produce a pellet of altered and aggregated cells at the bottom, leaving a clear supernatant. This supernatant is removed using a sterile, pyrogen-free pipette and placed in appropriate containers. It is extremely important not to contaminate the material at this point. The supernatant material (amebocyte lysate) may be stored at refrigeration temperatures (circa 45° F) for approximately 1 year without loss of activity, although slight precipitation of protein may occur. Note that all glassware with which Limulus amebocytes comes in contact are siliconized. However, the containers for storage of amebocyte lysate, the extract of Limulus amebocytes, does not have to be siliconized.

Amebocyte lysate may be standardized against any available endotoxin. For clinical use, the lysate should be sensitive enough to detect a final concentration of 0.00025 to 0.0005 ng/ml of E. Coli endotoxin (Difco).

EXAMPLE 1

One part of mammalian (human) blood plasma is diluted with 4 parts (v/v) of a solution of Owren's Buffer (0.028M sodium barbitol and 0.125 M sodium chloride) previously diluted with an equal volume of water. A test tube is charged with 0.9 ml. of the diluted plasma. To the charge there is added 0.2 ml. of an unknown liquid (a specimen of water for parenteral injection suspected of containing endotoxin), 0.2 ml. of reconstituted Platelet Factor Reagent lypholized (BBL division of Bioquest Division, Becton, Dickinson and Company, Cockeysville, Md.), and 0.3 ml. of lysate prepared according to the procedure of Preparation 2, supra. The resulting mixture is stirred thoroughly with a Vortex mixer. The mixture is then incubated at a temperature of 37° C. for 10 minutes. At the end of this period, 0.2 ml. of a solution of 0.025 M calcium chloride previously diluted in a ratio of ⅓ (v/v) with water is added to the incubate and the resulting mixture stirred with a Vortex mixer. The latter mixture is incubated at 37° C. for 25 minutes to obtain an agglomerate mass. The mass is disrupted by vigorous agitation with a Vortex mixer and the disrupted mixture centrifuged at 2500 RPM for 2 minutes. The resulting supernatant is decanted. To 0.1 ml. of the separated supernatant there is added with mixing 0.1 ml. of 0.025 M aqueous calcium chloride. To the resulting mixture there is added 0.1 ml. of whole mammalian (human) blood plasma, with mixing. After the last admixing, the clotting time of the resulting mixture is observed to positively coagulate in 45 seconds.

Following the above procedure but replacing the unknown liquid as used therein with an equal volume of a solution of 0.001 micrograms/ml. of E. Coli endotoxin (Difco Catalog No. 0127-B8) in saline, a positive control standard is obtained which coagulates 35 seconds after the final mixing of whole blood plasma.

Again following the above procedure but this time replacing the unknown liquid with an equal volume of normal saline, a negative control is prepared. The final mixture of the negative control obtained coagulates 25 seconds after final mixing.

In the example the positive control was 30 seconds and the negative control was 25 seconds, the positive is a 20% increase of the negative control. The value of the unknown (45 seconds) is an 80% increase of the negative control.

EXAMPLE 2

A test tube is charged with 0.3 ml. of the lysate prepared according to Preparation 2, supra, and diluted with 1.8 ml. of water (v/v), 0.2 ml. of lypholized Platelet Factor Reagent reconstituted with water (BBL, supra), 0.5 ml. of adsorbed mammalian (human) blood plasma (BBL, supra.) diluted in a ratio of 1/7 (v/v) with Owren's Buffer (previously diluted with an equal volume of water) and 0.5 ml. of an unknown blood serum specimen (human) previously treated with 3.8% Sodium Citrate (1:8; v/v) and diluted in a ratio of 1:10 (v/v) with Owren's Buffer as above, suspected of harboring endotoxins. The charge is mixed to obtain a homogeneous mixture with the aid of a Vortex mixer. The resulting mixture is incubated for 10 minutes at a temperature of 37° C. To the incubate there is added with stirring 0.2 ml. of 0.025 M calcium chloride previously diluted with water in a ratio of ⅓ (v/v). The resulting mixture is incubated for 15 minutes at a temperature of 37° C. and the resulting agglomeration is then disrupted by vigorous mixing with a Vortex mixer. The disrupted mixture is then centrifuged at 2500 RPM for 2 minutes and the supernatant decanted. To 0.1 milliliters of the supernatant there is added 0.1 milliliters of 0.025 M aqueous calcium chloride and then 0.1 milliliters of whole blood (human) plasma known to be free of endotoxin, with stirring. The coagulation time is recorded as 75 seconds.

Repeating the above procedure but replacing the unknown serum specimen as used therein with an equal volume of a known endotoxin containing reagent prepared by dissolving a nanogram of E. Coli endotoxin (Difco, supra) in 1 milliliter of endotoxin free blood serum (human) and diluting the solution with Owren's Buffer previously diluted with an equal volume of water in a ratio of 1 to 10 (v/v); a positive control is obtained with a clotting time of 80 seconds.

For a negative control, the above procedure is again repeated but this time replacing the unknown serum specimen with an equal volume of a known endotoxin free blood serum specimen, coagulation is observed after 60 seconds. In the above examples the positive control is 80 seconds and the negative control is 60 seconds. The positive control is a 33.3% increase over the negative control. The clotting time of the unknown is 75 seconds. This is a 25% increase above the negative control.

In carrying out the method of the invention, it will be obvious to those skilled in the art that all laboratory vessels, reagents and diluents or carriers should be free of prior contamination with endotoxins, with the exception of deliberate introduction of endotoxin in the preparation of the standards for comparison.

Those skilled in the art will also appreciate that many modifications of the method of the invention may be made without departing from the spirit and scope of the invention. For example, good laboratory procedure dictates that all determinations should be made in duplicate as a self-checking device and positive controls should be run simultaneously, i.e.; carrying out the steps of the method of the invention on a liquid known to contain endotoxins. In the event that such a control gives a result inconsistent with the positive or negative identification of endotoxin, the practitioner can check his technique, reagents, etc. or make further investigation.

What is claimed is:

1. A method of determining the presence or absence of endotoxins in liquids, which comprises:
   a. admixing 1 part by volume of mammalian blood plasma, 0.1 to 0.5 parts by volume of mammalian blood platelet factor reagent, 0.1 to 0.4 parts by volume of Limulus polyphemus amebocyte lysate and 0.1 to 0.5 parts by volume of the liquid for determination; said plasma being first diluted in a ratio of from 1:4 to 1:15 (v/v) with an aqueous buffer solution;
   b. incubating the mixture obtained in (a) above at 37° C. for 10 minutes;
   c. admixing a source of calcium ions with the incubated mixture of (b) above;
   d. incubating the mixture of (c) above at 37° C. for from 5 to 20 minutes;
   e. disrupting the mixture obtained by incubating in (d) above;
   f. separating solids from the disrupted mixture to obtain a supernatant;
   g. mixing aliquots of the supernatant, a source of calcium ions and mammalian blood plasma;
   h. measuring the elapsed time between completion of mixing in step (g) above and coagulation of the mixture obtained thereby; and
   i. comparing the elapsed time measured in step (h) above with the elapsed time measured after following the steps (a) through (h) above but replacing the liquid for determination added in step (a) with an equal proportion of a known endotoxin free solution.

2. A method according to claim 1 wherein said liquid is the blood serum of a mammal.

3. A method according to claim 1 wherein said plasma is diluted in a ratio of from 1:4 to 1:10 (v/v) with an aqueous buffer solution.

4. A method according to claim 1 wherein said separating is by the aid of centrifugal force.

5. A method according to claim 1 wherein said mixing of aliquots in step (g) comprises mixing about 0.1 to 0.5 ml. of a 0.001 to 0.5 molar solution of a calcium salt with 0.1 ml. of said supernatant.

6. A method of determining the presence or absence of endotoxins in blood serum, which comprises:
   a. admixing 1 part by volume of mammalian adsorbed blood plasma with 0.1 to 0.5 parts by volume of mammalian blood platelet factor reagent, 0.1 to 0.4 parts by volume of Limulus polyphemus amebocyte lysate and 0.1 to 0.5 parts by volume of a specimen of blood serum for determination; said plasma having been first diluted in a ratio of from 1:4 to 1:15 (v/v) with an aqueous buffer solution;
   b. incubating the mixture obtained in (a) above at 37° C. for 10 minutes;
   c. admixing a proportion of a source of calcium ions with the incubated mixture of (b) above;
   d. incubating the mixture of (c) above at 37° C. for from 15 to 25 minutes;
   e. disrupting the mixture obtained by incubating in (d) above;
   f. separating solids from the disrupted mixture to obtain a supernatant;
   g. mixing aliquots of the supernatant, a source of calcium ions and mammalian blood plasma;
   h. measuring the elapsed time between completion of mixing in step (g) above and coagulation of the mixture obtained thereby; and
   i. comparing the elapsed time with the elapsed time measured following the steps (a) through (h) above but replacing the liquid for determination added in step (a) with an equal proportion of a known endotoxin free blood serum.

7. A method according to claim 6 wherein step (c) comprises adding from 0.1 to 0.5 ml. of 0.001 to 0.5 molar calcium chloride for each ml. of diluted plasma added in step (a).

8. A method according to claim 6 wherein said separating is by the aid of centrifugal force.

9. A method according to claim 6 wherein said mixing of aliquots in step (g) comprises mixing about 0.1 to 0.5 ml. of a 0.001 to 0.5 molar solution of a calcium salt with 0.1 ml. of said supernatant.

* * * * *